(12) United States Patent
Renold et al.

(10) Patent No.: US 8,980,892 B2
(45) Date of Patent: *Mar. 17, 2015

(54) INSECTICIDAL COMPOUNDS

(75) Inventors: Peter Renold, Stein (CH); Thomas Pitterna, Stein (CH); Jerome Yves Cassayre, Stein (CH); Myriem El Qacemi, Stein (CH)

(73) Assignees: Syngenta Crop Protection LLC, Greensboro, NC (US); Syngenta Limited, Guildford, Surrey (GB)

( * ) Notice: Subject to any disclaimer, the term of this patent is extended or adjusted under 35 U.S.C. 154(b) by 168 days.

This patent is subject to a terminal disclaimer.

(21) Appl. No.: 13/260,499

(22) PCT Filed: Feb. 18, 2010

(86) PCT No.: PCT/EP2010/052056
§ 371 (c)(1),
(2), (4) Date: Sep. 26, 2011

(87) PCT Pub. No.: WO2010/108733
PCT Pub. Date: Sep. 30, 2010

(65) Prior Publication Data
US 2012/0015946 A1    Jan. 19, 2012

(30) Foreign Application Priority Data

| Mar. 26, 2009 | (GB) | 0905239.0 |
| Jun. 22, 2009 | (GB) | 0910767.3 |
| Jul. 24, 2009 | (WO) | PCT/EP2009/059563 |
| Feb. 17, 2010 | (EP) | 10153788 |

(51) Int. Cl.
| A01N 43/80 | (2006.01) |
| A01N 43/824 | (2006.01) |
| A01N 43/84 | (2006.01) |
| C07D 261/02 | (2006.01) |
| C07D 413/12 | (2006.01) |
| C07D 417/12 | (2006.01) |
| A01N 43/82 | (2006.01) |

(52) U.S. Cl.
CPC .............. *C07D 413/12* (2013.01); *A01N 43/82* (2013.01); *A01N 43/84* (2013.01); *A01N 43/80* (2013.01); *C07D 261/02* (2013.01); *C07D 417/12* (2013.01)
USPC ........ 514/236.8; 514/313; 514/314; 514/340; 514/363; 514/367; 514/371; 514/378; 544/137; 546/162; 546/171; 546/272.1; 548/139; 548/178; 548/195; 548/240

(58) Field of Classification Search
None
See application file for complete search history.

(56) References Cited

U.S. PATENT DOCUMENTS

| 4,066,770 A | 1/1978 | Boyce et al. |
| 6,313,147 B1 | 11/2001 | Shaber |
| 2009/0270407 A1 | 10/2009 | Tseng et al. |

FOREIGN PATENT DOCUMENTS

| EP | 0162383 | 11/1985 |
| WO | 2010/020522 | 2/2010 |

*Primary Examiner* — Alicia L Otton
(74) *Attorney, Agent, or Firm* — R. Kody Jones

(57) ABSTRACT

A compound of formula (I): wherein $A^1$, $A^2$, $A^3$, $A^4$, $G^1$, $R^1$, $R^2$, $R^3$, $R^4$, $R^{5a}$, $R^{5b}$ and $R^6$ are as defined in claim 1; or a salt or N-oxide thereof. Furthermore, the present invention relates to processes and intermediates for preparing compounds of formula (I), to insecticidal, acaricidal, nematicidal and molluscicidal compositions comprising the compounds of formula (I) and to methods of using the compounds of formula (I) to control insect, acarine, nematode and mollusc pests.

(I)

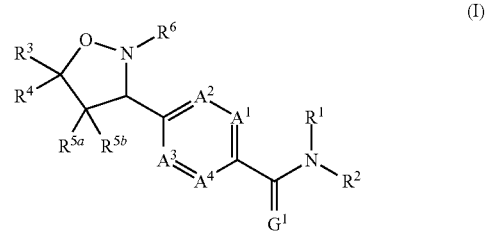

15 Claims, No Drawings

INSECTICIDAL COMPOUNDS

This application is a 371 of International Application No. PCT/EP2010/052056 filed Feb. 18, 2010, which claims priority to GB 0905239.0 filed Mar. 26, 2009, and GB 0910767.3 filed Jun. 22, 2009, and EP PCT/EP2009/059563 filed Jul. 24, 2009, and EP 10153788.4 filed Feb. 17, 2010, the contents of which are incorporated herein by reference.

The present invention relates to certain isoxazolidine derivatives, to processes and intermediates for preparing these derivatives, to insecticidal, acaricidal, nematicidal and molluscicidal compositions comprising these derivatives and to methods of using these derivatives to control insect, acarine, nematode and mollusc pests.

Certain isoxazoline derivatives with insecticidal properties are disclosed, for example, in EP 1,731,512.

It has now surprisingly been found that certain isoxazolidine derivatives have insecticidal properties.

The present invention therefore provides a compound of formula (I)

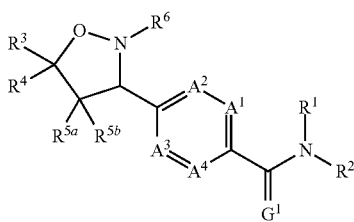

wherein $A^1$, $A^2$, $A^3$ and $A^4$ are independently of each other C—H, C—$R^7$, or nitrogen;

$G^1$ is oxygen or sulfur;

$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is $C_1$-$C_8$haloalkyl;

$R^4$ is aryl or aryl substituted by one to five $R^{11}$, or heteroaryl or heteroaryl substituted by one to five $R^{11}$;

$R^{5a}$ and $R^{5b}$ are both hydrogen;

$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$, aryl or aryl substituted by one to five $R^{14}$, or heterocyclyl or heterocyclyl substituted by one to five $R^{14}$;

each $R^7$ is independently halogen, cyano, nitro, $C_1$-$C_8$alkyl, $C_1$-$C_8$haloalkyl, $C_2$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkyl-sulfinyl-, $C_1$-$C_8$alkylsulfonyl-, or $C_1$-$C_8$haloalkylsulfonyl-;

each $R^8$ and $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;

each $R^9$ and $R^{13}$ is independently halogen or $C_1$-$C_8$alkyl;

each $R^{10}$, $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-; or a salt or N-oxide thereof.

The compounds of formula (I) may exist in different geometric or optical isomers or tautomeric forms. This invention covers all such isomers and tautomers and mixtures thereof in all proportions as well as isotopic forms such as deuterated compounds.

The compounds of the invention may contain one or more asymmetric carbon atoms, for example, at the —$CR^3R^4$— group and at the —$CR^{5a}R^{5a}$— group, an may exist as enantiomers (or as pairs of diastereoisomers) or as mixtures of such.

Alkyl groups (either alone or as part of a larger group, such as alkoxy-, alkylthio-, alkylsulfinyl-, alkylsulfonyl-, alkylcarbonyl- or alkoxycarbonyl-) can be in the form of a straight or branched chain and are, for example, methyl, ethyl, propyl, prop-2-yl, butyl, but-2-yl, 2-methyl-prop-1-yl or 2-methyl-prop-2-yl. The alkyl groups are preferably $C_1$-$C_6$, more preferably $C_1$-$C_4$, most preferably $C_1$-$C_3$ alkyl groups. Where an alkyl moiety is said to be substituted, the alkyl moiety is preferably substituted by one to four substituents, most preferably by one to three substituents.

Alkylene groups can be in the form of a straight or branched chain and are, for example, —$CH_2$—, —$CH_2$—$CH_2$—, —$CH(CH_3)$—, —$CH_2$—$CH_2$—$CH_2$—, —$CH(CH_3)$—$CH_2$—, or —$CH(CH_2CH_3)$—. The alkylene groups are preferably $C_1$-$C_3$, more preferably $C_1$-$C_2$, most preferably $C_1$ alkylene groups.

Alkenyl groups can be in the form of straight or branched chains, and can be, where appropriate, of either the (E)- or (Z)-configuration. Examples are vinyl and allyl. The alkenyl groups are preferably $C_2$-$C_6$, more preferably $C_2$-$C_4$, most preferably $C_2$-$C_3$ alkenyl groups.

Alkynyl groups can be in the form of straight or branched chains. Examples are ethynyl and propargyl. The alkynyl groups are preferably $C_2$-$C_6$, more preferably $C_2$-$C_4$, most preferably $C_2$-$C_3$ alkynyl groups.

Halogen is fluorine, chlorine, bromine or iodine.

Haloalkyl groups (either alone or as part of a larger group, such as haloalkoxy-, haloalkylthio-, haloalkylsulfinyl- or haloalkylsulfonyl-) are alkyl groups which are substituted by one or more of the same or different halogen atoms and are, for example, difluoromethyl, trifluoromethyl, chlorodifluoromethyl or 2,2,2-trifluoro-ethyl.

Haloalkenyl groups are alkenyl groups which are substituted by one or more of the same or different halogen atoms and are, for example, 2,2-difluoro-vinyl or 1,2-dichloro-2-fluoro-vinyl.

Haloalkynyl groups are alkynyl groups which are substituted by one or more of the same or different halogen atoms and are, for example, 1-chloro-prop-2-ynyl.

Cycloalkyl groups or carbocyclic rings can be in mono- or bi-cyclic form and are, for example, cyclopropyl, cyclobutyl, cyclohexyl and bicyclo[2.2.1]heptan-2-yl. The cycloalkyl groups are preferably $C_3$-$C_8$, more preferably $C_3$-$C_6$ cycloalkyl groups. Where a cycloalkyl moiety is said to be substituted, the cycloalkyl moiety is preferably substituted by one to four substituents, most preferably by one to three substituents.

Aryl groups (either alone or as part of a larger group, such as aryl-alkylene-) are aromatic ring systems which can be in mono-, bi- or tricyclic form. Examples of such rings include phenyl, naphthyl, anthracenyl, indenyl or phenanthrenyl. Preferred aryl groups are phenyl and naphthyl, phenyl being most preferred. Where an aryl moiety is said to be substituted, the aryl moiety is preferably substituted by one to four substituents, most preferably by one to three substituents.

Heteroaryl groups (either alone or as part of a larger group, such as heteroaryl-alkylene-) are aromatic ring system containing at least one heteroatom and consisting either of a single ring or of two or more fused rings. Preferably, single rings will contain up to three heteroatoms and bicyclic systems up to four heteroatoms which will preferably be chosen from nitrogen, oxygen and sulfur. Examples of monocyclic groups include pyridyl, pyridazinyl, pyrimidinyl, pyrazinyl, pyrrolyl, pyrazolyl, imidazolyl, triazolyl, furanyl, thiophenyl, oxazolyl, isoxazolyl, oxadiazolyl, thiazolyl, isothiazolyl and thiadiazolyl. Examples of bicyclic groups include quinolinyl, cinnolinyl, quinoxalinyl, indolyl, indazolyl, benzimidazolyl, benzothiophenyl and benzothiazolyl. Monocyclic heteroaryl groups are preferred, pyridyl being most preferred. Where a heteroaryl moiety is said to be substituted, the heteroaryl moiety is preferably substituted by one to four substituents, most preferably by one to three substituents.

Heterocyclyl groups or heterocyclic rings (either alone or as part of a larger group, such as heterocyclyl-alkylene-) are defined to include heteroaryl groups and in addition their unsaturated or partially unsaturated analogues. Examples of monocyclic groups include thietanyl, pyrrolidinyl, tetrahydrofuranyl, [1,3]dioxolanyl, piperidinyl, piperazinyl, [1,4]dioxanyl, and morpholinyl or their oxidised versions such as 1-oxo-thietanyl and 1,1-dioxo-thietanyl. Examples of bicyclic groups include 2,3-dihydro-benzofuranyl, benzo[1,3]dioxolanyl, and 2,3-dihydro-benzo[1,4]dioxinyl. Where a heterocyclyl moiety is said to be substituted, the heterocyclyl moiety is preferably substituted by one to four substituents, most preferably by one to three substituents.

Preferred values of $A^1$, $A^2$, $A^3$, $A^4$, $G^1$, $R^1$, $R^2$, $R^3$, $R^4$, $R^6$, $R^7$, $R^8$, $R^9$, $R^{10}$, $R^{11}$, $R^{12}$, $R^{13}$, $R^{14}$ and $R^{15}$ are, in any combination, as set out below.

Preferably no more than two of $A^1$, $A^2$, $A^3$ and $A^4$ are nitrogen.

Preferably $A^1$ is C—H or C—$R^7$, most preferably $A^1$ is C—$R^7$.

Preferably $A^2$ is C—H or C—$R^7$, most preferably $A^2$ is C—H.

Preferably $A^3$ is C—H or C—$R^7$, most preferably $A^3$ is C—H.

Preferably $A^4$ is C—H or C—$R^7$, most preferably $A^4$ is C—H.

In one preferred group of compounds $A^1$ is C—$R^7$, $A^2$ is C—H, $A^3$ is C—H or nitrogen and $A^4$ is C—H or nitrogen.

In another group of preferred compounds $A^1$ is C—$R^7$, $A^2$ is C—H, $A^3$ is C—H and $A^4$ is C—H.

Preferably $G^1$ is oxygen.

Preferably $R^1$ is hydrogen, methyl, ethyl, methylcarbonyl-, or methoxycarbonyl-, more preferably hydrogen, methyl or ethyl, most preferably hydrogen.

Preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, pyridazinyl, pyrimidinyl, pyrazinyl, pyrrolyl, pyrazolyl, imidazolyl, triazolyl, tetrazolyl, tetrahydrothiophenyl, furanyl, thiophenyl, oxazolyl, isoxazolyl, oxadiazolyl, thiazolyl, isothiazolyl, thiadiazolyl, quinolinyl, cinnolinyl, quinoxalinyl, indolyl, indazolyl, benzimidazolyl, benzothiophenyl, benzothiazolyl, oxetanyl, thietanyl, oxo-thietanyl, dioxo-thietanyl, pyrrolidinyl, tetrahydrofuranyl, [1,3]dioxolanyl, piperidinyl, piperazinyl, [1,4]dioxanyl, and morpholinyl, 2,3-dihydro-benzofuranyl, benzo[1,3]dioxolanyl, and 2,3-dihydro-benzo[1,4]dioxinyl.

More preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, tetrahydrofuranyl, imidazolyl, pyrazolyl, pyrrolyl, thiazolyl, oxetanyl, thietanyl, oxo-thietanyl and dioxo-thietanyl.

More preferably still $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-

$C_4$alkylene- or pyridyl-$C_1$-$C_4$alkylene- wherein the pyridyl moiety is substituted by one to four $R^{10}$, tetrahydrofuranyl-$C_1$-$C_4$alkylene- or tetrahydrofuranyl-$C_1$-$C_4$alkylene- wherein the tetrahydrofuranyl moiety is substituted by one to five $R^{10}$, imidazolyl-$C_1$-$C_4$alkylene- or imidazolyl-$C_1$-$C_4$alkylene- wherein the imidazolyl moiety is substituted by one to three $R^{10}$, pyrazolyl-$C_1$-$C_4$alkylene- or pyryazolyl-$C_1$-$C_4$alkylene- wherein the pyrazolyl moiety is substituted by one to three $R^{10}$, pyrrolyl-$C_1$-$C_4$alkylene- or pyrrolyl-$C_1$-$C_4$alkylene- wherein the pyrrolyl moiety is substituted by one to four $R^{10}$, thiazolyl-$C_1$-$C_4$alkylene- or thiazolyl-$C_1$-$C_4$alkylene- wherein the thiazolyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, for example $C_1$-$C_8$alkyl or $C_1$-$C_8$alkyl substituted by one to five $R^8$, $C_3$-$C_{10}$cyclo-alkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, tetrahydrofuranyl-$C_1$-$C_4$alkylene- or tetrahydrofuranyl-$C_1$-$C_4$alkylene- wherein the tetrahydrofuranyl moiety is substituted by one to five $R^{10}$, imidazolyl-$C_1$-$C_4$alkylene- or imidazolyl-$C_1$-$C_4$alkylene- wherein the imidazolyl moiety is substituted by one to three $R^{10}$, pyrazolyl-$C_1$-$C_4$alkylene- or pyryazolyl-$C_1$-$C_4$alkylene- wherein the pyrazolyl moiety is substituted by one to three $R^{10}$, pyrrolyl-$C_1$-$C_4$alkylene- or pyrrolyl-$C_1$-$C_4$alkylene- wherein the pyrrolyl moiety is substituted by one to four $R^{10}$, thiazolyl-$C_1$-$C_4$alkylene- or thiazolyl-$C_1$-$C_4$alkylene- wherein the thiazolyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$.

Even more preferably $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, for example $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$, more preferably $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl, dioxo-thietanyl, $C_1$-$C_8$alkylaminocarbonyl-methylene, $C_1$-$C_8$haloalkylaminocarbonyl-methylene, or $C_3$-$C_8$cycloalkyl-aminocarbonyl-methylene, for example $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to four $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl or dioxo-thietanyl, most preferably butyl-, cyclobutyl-, 1-phenyl-eth-1-yl-, phenyl-methyl-, (pyrid-2-yl)-methyl-, thietanyl-, oxo-thietanyl- or dioxo-thietanyl-.

A group of preferred compounds are those wherein $R^2$ is $C_1$-$C_6$alkyl or $C_1$-$C_6$alkyl substituted by one to five $R^8$, for example ethyl-, butyl-, but-2-yl-, 3-bromo-propyl-, 2,2,2-trifluoro-ethyl-, 3,3,3-trifluoro-propyl-, 2-methoxy-ethyl-, and 1-methoxy-prop-2-yl-.

A group of preferred compounds are those wherein $R^2$ is $C_3$-$C_8$cycloalkyl or $C_3$-$C_8$cycloalkyl substituted by one to five $R^9$, for example cyclobutyl-, and 2-methyl-cyclohex-1-yl-.

A group of preferred compounds are those wherein $R^2$ is aryl-$C_1$-$C_2$alkylene- or aryl-$C_1$-$C_2$alkylene- wherein the aryl moiety is substituted by one to five $R^{10}$, for example phenyl-methyl-, 1-phenyl-eth-1-yl-, 2-phenyl-eth-1-yl-, (3-chloro-phenyl)-methyl-, (2-fluoro-phenyl)-methyl-, (4-methoxy-phenyl)-methyl-, (2-trifluoromethyl-phenyl)-methyl-, and (2-trifluoromethoxy-phenyl)-methyl-.

A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^{10}$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl. A group of preferred compounds are those wherein $R^2$ is heterocyclyl-$C_1$-$C_2$alkylene- or heterocyclyl-$C_1$-$C_2$alkylene- wherein the heterocyclyl moiety is substituted by one to five $R^{10}$, for example (pyrid-2-yl)-methyl-, (pyrid-3-yl)-methyl-, (2-chloro-pyrid-5-yl)-methyl-, (1-methyl-1H-imidazol-4-yl)-methyl-, (furan-2-yl)-methyl-, 2-(thiophen-2'-yl)-eth-1-yl-, 2-(indol-3'-yl)-eth-1-yl-, (1H-benzimidazol-2-yl)-methyl-, (oxetan-2-yl)-methyl-, (tetrahydrofuran-2-yl)-methyl-, 2-([1',3']dioxolan-2'-yl)-eth-1-yl-, 2-(morpholin-4'-yl)-eth-1-yl-, 2-(benzo[1',3']dioxol-5'-yl)-eth-1-yl-, and (2,3-dihydro-benzo[1,4]dioxin-6-yl)-methyl-, more preferably $R^2$ is heteroaryl-$C_1$-$C_2$alkylene- or heteroaryl-$C_1$-$C_2$alkylene- wherein the heteroaryl moiety is substituted by one to five $R^{10}$. A group of preferred compounds are those wherein $R^2$ is aryl or aryl substituted by one to five $R^{10}$, for example 2-chloro-phenyl-, 3-fluoro-phenyl-, 2-methyl-phenyl-, 2-chloro-6-methyl-phenyl-, 2-trifluoromethyl-phenyl-, and 2,4-dimethoxy-phenyl-.

A group of preferred compounds are those wherein $R^2$ is heterocyclyl- or heterocyclyl substituted by one to five $R^{10}$ in which the heterocyclyl group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

A group of preferred compounds are those wherein $R^2$ is heterocyclyl or heterocyclyl substituted by one to five $R^{10}$, for example 3-methyl-pyrid-2-yl-, 1,3-dimethyl-1H-pyrazol-5-yl-, 4-methyl-thiazol-2-yl-, 5-methyl-thiadiazol-2-yl-, quinolin-2-yl-, quinolin-5-yl-, benzothiazol-6-yl-, 4-methyl-benzothiazol-2-yl-, thietan-3-yl-, 1-oxo-thietan-3-yl-, 1,1-di-oxo-thietan-3-yl-, and 3-methyl-thietan-3-yl-, more preferably $R^2$ is oxetanyl, thietanyl, oxo-thietanyl or dioxo-thietanyl each optionally substituted by one to five $R^{10}$, most preferably $R^2$ is thietanyl, oxo-thietanyl or dioxo-thietanyl each optionally substituted by one to five $R^{10}$. It is particularly preferred that the oxetanyl, thietanyl, oxo-thietanyl or dioxo-thietanyl ring is linked via the 3-position.

Preferably $R^3$ is chlorodifluoromethyl or trifluoromethyl, most preferably trifluoro-methyl.

Preferably $R^4$ is aryl or aryl substituted by one to five $R^{11}$, more preferably aryl substituted by one to three $R^{11}$, more preferably phenyl substituted by one to three $R^{11}$, even more preferably 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl-, most preferably $R^4$ is 3,5-dichloro-phenyl.

Preferably $R^6$ is $C_1$-$C_8$alkyl or $C_1$-$C_8$alkyl substituted by one to five $R^{12}$, aryl-$C_1$-$C_4$alkylene- or aryl-$C_1$-$C_4$alkylene- wherein the aryl moiety is substituted by one to five $R^{14}$, heteroaryl-$C_1$-$C_4$alkylene- or heteroaryl-$C_1$-$C_4$alkylene- wherein the heteroaryl moiety is substituted by one to five $R^{14}$, more preferably $C_1$-$C_8$alkyl or $C_1$-$C_8$alkyl substituted by one to five $R^{12}$, phenyl-$C_1$-$C_4$alkylene- or phenyl-$C_1$-$C_4$alkylene- wherein the phenyl moiety is substituted by one to five $R^{14}$, more preferably $C_1$-$C_8$alkyl or $C_1$-$C_8$alkyl substituted by one to five $R^{12}$, phenyl-methylene- or phenyl-methylene wherein the phenyl moiety is substituted by one to five $R^{14}$, more preferably $C_1$-$C_8$alkyl or phenyl-methylene, more preferably $C_1$-$C_8$alkyl, more preferably methyl.

Preferably each $R^7$ is independently halogen, cyano, nitro, $C_1$-$C_8$alkyl, $C_1$-$C_8$halo-alkyl, $C_1$-$C_8$alkenyl, $C_1$-$C_8$haloalkenyl, $C_1$-$C_8$alkoxy-, or $C_1$-$C_8$haloalkoxy-, more preferably bromo, chloro, fluoro, cyano, nitro, methyl, ethyl, trifluoromethyl, vinyl, methoxy, difluoromethoxy, or trifluoromethoxy, most preferably methyl.

Preferably each $R^8$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^9$ is independently chloro, fluoro or methyl, most preferably methyl.

Preferably each $R^{10}$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^{11}$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-, more preferably bromo, chloro, fluoro, trifluoromethyl, methoxy, or methylthio, most preferably bromo or chloro.

Preferably each $R^{12}$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-, more preferably bromo, chloro, fluoro, methoxy, or methylthio, most preferably chloro, fluoro, or methoxy.

Preferably each $R^{13}$ is independently chloro, fluoro or methyl, most preferably methyl.

Preferably each $R^{14}$ is independently halogen, cyano, nitro, $C_1$-$C_8$alkyl, $C_1$-$C_8$haloalkyl, $C_1$-$C_8$alkoxy-, $C_1$-$C_8$haloalkoxy-, more preferably bromo, chloro, fluoro, cyano, nitro, methyl, ethyl, trifluoromethyl, methoxy, difluoromethoxy, or trifluoromethoxy, most preferably bromo, chloro, fluoro, cyano or methyl.

Preferably each $R^{15}$ is independently bromo, chloro, fluoro, cyano, nitro, methyl, ethyl, trifluoromethyl, methoxy, difluoromethoxy, or trifluoromethoxy, more preferably bromo, chloro, fluoro, nitro, or methyl, most preferably chloro, fluoro, or methyl.

A group of preferred compounds are those wherein
$A^1$, $A^2$, $A^3$ and $A^4$ are independently of each other C—H, C—$R^7$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, or heterocyclyl or heterocyclyl substituted by one to five $R^{10}$;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^{5a}$ and $R^{5b}$ are both hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$, aryl or aryl substituted by one to five $R^{14}$, or heterocyclyl or heterocyclyl substituted by one to five $R^{14}$;
each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^8$ and $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^9$ and $R^{13}$ is independently halogen or $C_1$-$C_8$alkyl;
each $R^{10}$, $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;
each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-.

Another group of preferred compounds are those wherein
$A^1$ is C—$R^7$, $A^2$ is C—H, $A^3$ is C—H or nitrogen and $A^4$ is C—H or nitrogen;
$G^1$ is oxygen;
$R^1$ is hydrogen, methyl, ethyl, methylcarbonyl-, or methoxycarbonyl-;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from pyridyl, tetrahydrofuranyl, imidazolyl, pyrazolyl, pyrrolyl, thiazolyl, oxetanyl, thietanyl, oxo-thietanyl and dioxo-thietanyl;

$R^3$ is $C_1$-$C_8$ haloalkyl;

$R^4$ is phenyl substituted by one to three $R^{11}$;

$R^{5a}$ and $R^{5b}$ are hydrogen;

$R^6$ is $C_1$-$C_8$alkyl or $C_1$-$C_8$alkyl substituted by one to five $R^{12}$, aryl-$C_1$-$C_4$alkylene- or aryl-$C_1$-$C_4$alkylene- wherein the aryl moiety is substituted by one to five $R^{14}$, heteroaryl-$C_1$-$C_4$alkylene- or heteroaryl-$C_1$-$C_4$alkylene- wherein the heteroaryl moiety is substituted by one to five $R^{14}$;

$R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkoxy-, or $C_1$-$C_8$haloalkoxy-;

each $R^8$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-;

each $R^9$ is independently chloro, fluoro or methyl;

each $R^{10}$ is independently halogen, cyano, nitro, $C_1$-$C_8$alkyl, $C_1$-$C_8$haloalkyl, $C_1$-$C_8$alkoxy-, $C_1$-$C_8$haloalkoxy-;

each $R^{11}$ is independently halogen, $C_1$-$C_8$alkyl, $C_1$-$C_8$haloalkyl, $C_1$-$C_8$alkoxy-, $C_1$-$C_8$haloalkoxy-, $C_1$-$C_8$alkylthio-, or $C_1$-$C_8$haloalkylthio-;

each $R^{12}$ is independently halogen, cyano, nitro, hydroxy, $C_1$-$C_8$alkoxy-, $C_1$-$C_8$haloalkoxy-, mercapto, $C_1$-$C_8$alkylthio-, $C_1$-$C_8$haloalkylthio-;

each $R^{14}$ is independently halogen, cyano, nitro, $C_1$-$C_8$alkyl, $C_1$-$C_8$haloalkyl, $C_1$-$C_8$alkoxy-, $C_1$-$C_8$haloalkoxy-;

Yet another group of preferred compounds are those wherein $A^1$ is C—$R^7$, $A^2$ is C—H, $A^3$ is C—H and $A^4$ is C—H;

$G^1$ is oxygen;

$R^1$ is hydrogen, methyl or ethyl;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is chlorodifluoromethyl or trifluoromethyl;

$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl- $R^{5a}$ and $R^{5b}$ are hydrogen;

$R^6$ is $C_1$-$C_8$alkyl or $C_1$-$C_8$alkyl substituted by one to five $R^{12}$, phenyl-$C_1$-$C_4$alkylene- or phenyl-$C_1$-$C_4$alkylene- wherein the phenyl moiety is substituted by one to five $R^{14}$, $R^7$ is independently bromo, chloro, fluoro, cyano, nitro, methyl, ethyl, trifluoromethyl, vinyl, methoxy, difluoromethoxy, or trifluoromethoxy;

each $R^8$ is independently bromo, chloro, fluoro, methoxy, or methylthio;

each $R^9$ is methyl;

each $R^{10}$ is independently bromo, chloro, fluoro, cyano, nitro, methyl, ethyl, trifluoromethyl, methoxy, difluoromethoxy, or trifluoromethoxy;

each $R^{12}$ is independently bromo, chloro, fluoro, methoxy, or methylthio;

each $R^{14}$ is independently bromo, chloro, fluoro, cyano, nitro, methyl, ethyl, trifluoromethyl, methoxy, difluoromethoxy, or trifluoromethoxy.

A further group of preferred compounds are those wherein $A^1$ is C—$R^7$, $A^2$ is C—H, $A^3$ is C—H and $A^4$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl or dioxo-thietanyl;

$R^3$ is trifluoromethyl;

$R^4$ is 3,5-dichloro-phenyl;

$R^{5a}$ and $R^{5b}$ are hydrogen;

$R^6$ is $C_1$-$C_8$alkyl;

$R^7$ is methyl each $R^{10}$ is independently bromo, chloro, fluoro, cyano or methyl.

A further group of preferred compounds are those wherein $A^1$ is C—$R^7$, $A^2$ is CH, $A^3$ is CH and $A^4$ is CH;

$G^1$ is oxygen;

$R^1$ is hydrogen;

$R^2$ is $C_2$-$C_6$alkyl or $C_2$-$C_6$alkyl substituted by one to three halogen atoms, $C_4$-$C_8$cycloalkyl or $C_4$-$C_8$cycloalkyl substituted by one or two methyl groups, phenyl-$C_1$-$C_2$alkylene- or phenyl-$C_1$-$C_2$alkylene- wherein the phenyl moiety is substituted by one to five $R^{10}$, pyridyl-$C_1$-$C_2$alkylene- or pyridyl-$C_1$-$C_2$alkylene- wherein the pyridyl moiety is substituted by one to four $R^{10}$, thietanyl, oxo-thietanyl or dioxo-thietanyl;

$R^3$ is trifluoromethyl;

$R^4$ is 3,5-dichloro-phenyl;

$R^{5a}$ and $R^{5b}$ are hydrogen;

$R^6$ is $C_1$-$C_8$alkyl;

$R^7$ is methyl each $R^{10}$ is independently bromo, chloro, fluoro, cyano or methyl.

In one embodiment the present invention provides compounds of formula (Ia)

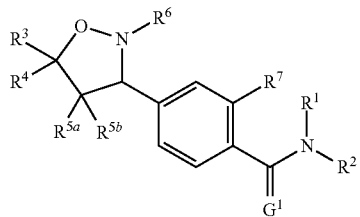

(Ia)

wherein $G^1$, $R^1$, $R^2$, $R^3$, $R^4$, $R^{5a}$, $R^{5b}$, $R^6$ and $R^7$ are as defined for compounds of formula (I); or a salt or N-oxide thereof. The preferences for $G^1$, $R^1$, $R^2$, $R^3$, $R^4$, $R^{5a}$, $R^{5b}$, $R^6$ and $R^7$ are the same as the preferences set out for the corresponding substituents of compounds of the formula (I).

Certain intermediates are novel and as such form a further aspect of the invention. One group of novel intermediates are compounds of formula (II)

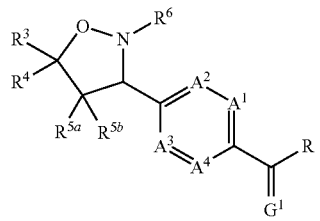

(II)

wherein $A^1$, $A^2$, $A^3$, $A^4$, $R^3$, $R^4$, $R^{5a}$, $R^{5b}$ and $R^6$ are as defined for a compound of formula (I), $G^1$ is oxygen, and R is hydroxy, $C_1$-$C_6$alkoxy or halogen, such as bromo, chloro or fluoro; or a salt or N-oxide thereof. The preferences for $A^1$, $A^2$, $A^3$, $A^4$, $R^3$, $R^4$, $R^{5a}$, $R^{5b}$ and $R^6$ are the same as the preferences set out for the corresponding substituents of a compound of formula (I). Preferably R is hydroxy, $C_1$-$C_6$alkoxy or chloro.

The compounds in Table 1 below illustrate the compounds of the invention.

TABLE 1

Table 1 provides 50 compounds of formula (Ia) wherein $G^1$ is oxygen, $R^3$ is trifluoromethyl, $R^4$ is 3,5-dichloro-phenyl-, $R^{5a}$ and $R^{5b}$ are both hydrogen, $R^6$ and $R^7$ are both methyl, and $R^1$ and $R^2$ have the values listed in the table below.

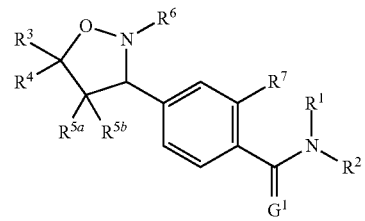

(Ia)

| Compound numbers | $R^1$ | $R^2$ |
|---|---|---|
| 1.01 | H | ethyl- |
| 1.02 | H | butyl- |
| 1.03 | H | but-2-yl- |

TABLE 1-continued

Table 1 provides 50 compounds of formula (Ia) wherein $G^1$ is oxygen, $R^3$ is trifluoromethyl, $R^4$ is 3,5-dichloro-phenyl-, $R^{5a}$ and $R^{5b}$ are both hydrogen, $R^6$ and $R^7$ are both methyl, and $R^1$ and $R^2$ have the values listed in the table below.

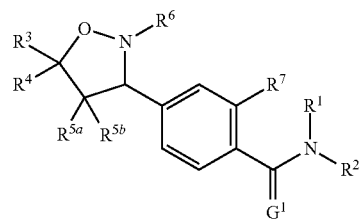

(Ia)

| Compound numbers | $R^1$ | $R^2$ |
|---|---|---|
| 1.04 | H | 3-bromo-propyl- |
| 1.05 | H | 2,2,2-trifluoro-ethyl- |
| 1.06 | H | 3,3,3-trifluoro-propyl- |
| 1.07 | H | 2-methoxy-ethyl- |
| 1.08 | H | 1-methoxy-prop-2-yl- |
| 1.09 | H | cyclobutyl- |
| 1.10 | H | 2-methyl-cyclohex-1-yl- |
| 1.11 | H | phenyl-methyl- |
| 1.12 | H | 1-phenyl-eth-1-yl- |
| 1.13 | H | 2-phenyl-eth-1-yl- |
| 1.14 | H | (3-chloro-phenyl)-methyl- |
| 1.15 | H | (2-fluoro-phenyl)-methyl- |
| 1.16 | H | (4-methoxy-phenyl)-methyl- |
| 1.17 | H | (2-trifluoromethyl-phenyl)-methyl- |
| 1.18 | H | (2-trifluoromethoxy-phenyl)-methyl- |
| 1.19 | H | (pyrid-2-yl)-methyl- |
| 1.20 | H | (pyrid-3-yl)-methyl- |
| 1.21 | H | (2-chloro-pyrid-5-yl)-methyl- |
| 1.22 | H | (1-methyl-1H-imidazol-4-yl)-methyl- |
| 1.23 | H | (furan-2-yl)-methyl- |
| 1.24 | H | 2-(thiophen-2'-yl)-eth-1-yl- |
| 1.25 | H | 2-(indol-3'-yl)-eth-1-yl- |
| 1.26 | H | (1H-benzimidazol-2-yl)-methyl- |
| 1.27 | H | (oxetan-2-yl)-methyl- |
| 1.28 | H | (tetrahydrofuran-2-yl)-methyl- |
| 1.29 | H | 2-([1',3']dioxolan-2'-yl)-eth-1-yl- |
| 1.30 | H | 2-(morpholin-4'-yl)-eth-1-yl- |
| 1.31 | H | 2-(benzo([1',3']dioxol-5'-yl)-eth-1-yl- |
| 1.32 | H | (2,3-dihydro-benzo[1,4]dioxin-6-yl)-methyl- |
| 1.33 | H | 2-chloro-phenyl- |
| 1.34 | H | 3-fluoro-phenyl- |
| 1.35 | H | 2-methyl-phenyl- |
| 1.36 | H | 2-chloro-6-methyl-phenyl- |
| 1.37 | H | 2-trifluoromethyl-phenyl- |
| 1.38 | H | 2,4-dimethoxy-phenyl- |
| 1.39 | H | 3-methyl-pyrid-2-yl- |
| 1.40 | H | 1,3-dimethyl-1H-pyrazol-5-yl- |
| 1.41 | H | 4-methyl-thiazol-2-yl- |
| 1.42 | H | 5-methyl-thiadiazol-2-yl- |
| 1.43 | H | quinolin-2-yl- |
| 1.44 | H | quinolin-5-yl- |
| 1.45 | H | benzothiazol-6-yl- |
| 1.46 | H | 4-methyl-benzothiazol-2-yl- |
| 1.47 | H | thietan-3-yl- |
| 1.48 | H | 1-oxo-thietan-3-yl- |
| 1.49 | H | 1,1-dioxo-thietan-3-yl- |
| 1.50 | H | 3-methyl-thietan-3-yl- |

The compounds of the invention may be made by a variety of methods as shown in Scheme 1.

Scheme 1

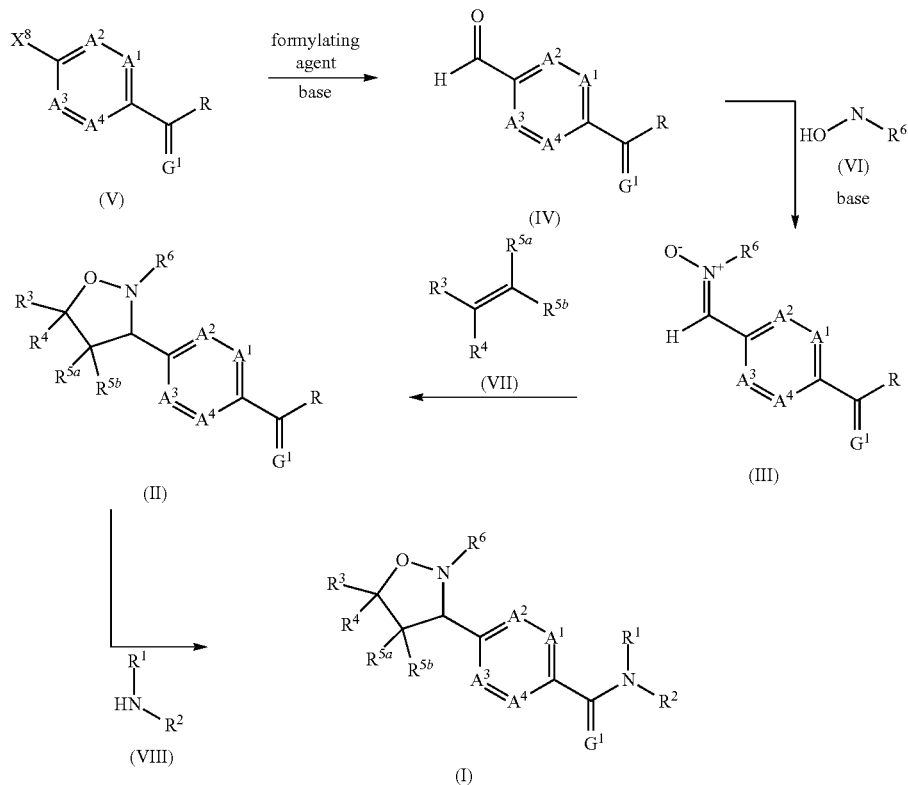

1) Compounds of formula (I) wherein $G^1$ is oxygen, can be prepared by treating an acid derivative of formula (II) wherein $G^1$ is oxygen and R is OH, $C_1$-$C_6$alkoxy or Cl, F or Br, with an amine of the formula (VIII) wherein $R^1$ and $R^2$ are as defined for a compound of formula (I) as shown in Scheme 1. When R is OH such reactions are usually carried out in the presence of a coupling reagent, such as N,N'-dicyclohexylcarbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (VIII) are known in the literature or can be prepared using methods known to a person skilled in the art.

2) Acid halides of formula (II), wherein $G^1$ is oxygen and R is Cl, F or Br, may be made from carboxylic acids of formula (II), wherein $G^1$ is oxygen and R is OH, under standard conditions, such as treatment with thionyl chloride or oxalyl chloride. A preferred solvent is dichloromethane. The reaction is carried out at a temperature of from 0° C. to 100° C., preferably from 15° C. to 30° C., in particular at ambient temperature.

3) Carboxylic acids of formula (II), wherein $G^1$ is oxygen and R is OH, may be formed from esters of formula (II), wherein $G^1$ is oxygen and R is $C_1$-$C_6$alkoxy. It is known to a person skilled in the art that there are many methods for the hydrolysis of such esters depending on the nature of the alkoxy group. One widely used method to achieve such a transformation is the treatment of the ester with an alkali hydroxide, such as lithium hydroxide, sodium hydroxide or potassium hydroxide, in a solvent, such as ethanol or tetrahydrofuran, in the presence of water. Another is the treatment of the ester with an acid, such as trifluoroacetic acid, in a solvent, such as dichloromethane, followed by addition of water. The reaction is carried out at a temperature of from 0° C. to 150° C., preferably from 15° C. to 100° C., in particular at ambient temperature.

4) Compounds of formula (II) wherein $G^1$ is oxygen and R is $C_1$-$C_6$alkoxy, such as methoxy or tert-butoxy, can be prepared by reaction of a nitrone of formula (III) wherein $G^1$ is oxygen and R is $C_1$-$C_6$alkoxy, such as methoxy or tert-butoxy, with a vinyl compound of formula (VII) wherein $R^3$, $R^4$, $R^{5a}$ and $R^{5b}$ are as defined for a compound of formula (I). The reaction is carried out optionally in the presence of a solvent, for example a non-polar solvent, such as toluene. The reaction is carried out at a temperature of from 0° C. to 150° C., preferably from 100° C. to 120° C. The reaction can conveniently be carried out in a microwave. Vinyl compounds of formula (VII) are commercially available or can be made by methods known to a person skilled in the art.

5) Compounds of formula (III) wherein $G^1$ is oxygen and R is $C_1$-$C_6$alkoxy, such as methoxy or tert-butoxy, can be made by reaction of an aldehyde of formula (IV) wherein $G^1$ is oxygen and R is $C_1$-$C_6$alkoxy, such as methoxy or tert-butoxy, with an N-substituted hydroxylamine of the formula (VI) wherein $R^6$ is as defined for a compound of formula (I), such as N-methylhydroxylamine hydrochloride. The reaction is carried out in the presence of a base, for example an organic base, such as triethylamine or sodium acetate, or an inorganic base, such as sodium hydrogen carbonate, in the presence of a solvent, for example a polar solvent, such as tetrahydrofuran, or water, or a mixture thereof. The reaction is carried out at a temperature of from 0° C. to 100° C., preferably from 15° C. to 50° C., in particular at ambient temperature. N-Substituted hydroxylamines of formula (VI) are commercially available or can be made by methods known to a person skilled in the art.

6) Compounds of formula (IV) wherein $G^1$ is oxygen and R is $C_1$-$C_6$alkoxy, such as methoxy or tert-butoxy, can be prepared by reaction of a compound of formula (V) wherein $G^1$ is oxygen and R is $C_1$-$C_6$alkoxy, for example methoxy or tert-butoxy, and $X^B$ is a leaving group, for example a halogen, such as bromo, with a formylating agent, such as N,N-dimethylformamide. The reaction is carried out in the presence of a base, for example a lithium base, such as butyl lithium, in the presence of a solvent, for example a polar solvent, such as tetrahydrofuran or excess N,N-dimethylformamide. The reaction is carried out at a temperature of from −200° C. to 0° C., preferably from −150° C. to −50° C., in particular at −100° C. Compounds of formula (V) are commercially available or can be made by methods known to a person skilled in the art.

7) Compounds of formula (I) wherein $G^1$ is sulfur, may be made by treatment of a compound of formula (II), wherein $G^1$ is oxygen and R is OH, $C_1$-$C_6$alkoxy or Cl, F or Br, with a thio-transfer reagent such as Lawesson's reagent or phosphorus pentasulfide prior to elaborating to compounds of formula (I), as described under 1).

The compounds of formula (I) can be used to control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be controlled by the use of the invention compounds include those pests associated with agriculture (which term includes the growing of crops for food and fiber products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

The compounds of the invention may be used for example on turf, ornamentals, such as flowers, shrubs, broad-leaved trees or evergreens, for example conifers, as well as for tree injection, pest management and the like.

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotermitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulfureus*), *Solenopsis geminata* (fire ant), *Monomorium pharaonis* (pharaoh's ant), *Damalinia* spp. and *Linognathus* spp. (biting and sucking lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp. (citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of controlling insects, acarines, nematodes or molluscs which comprises applying an insecticidally, acaricidally, nematicidally or molluscicidally effective amount of a compound of formula (I), or a composition containing a compound of formula (I), to a pest, a locus of pest, preferably a plant, or to a plant susceptible to attack by a pest. The compounds of formula (I) are preferably used against insects or acarines.

The term "plant" as used herein includes seedlings, bushes and trees.

Crops are to be understood as also including those crops which have been rendered tolerant to herbicides or classes of herbicides (e.g. ALS-, GS-, EPSPS-, PPO- and HPPD-inhibitors) by conventional methods of breeding or by genetic engineering. An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®.

Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood as being those which are obtained by conventional methods of breeding or genetic engineering and contain so-called output traits (e.g. improved storage stability, higher nutritional value and improved flavor).

In order to apply a compound of formula (I) as an insecticide, acaricide, nematicide or molluscicide to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a compound of formula (I) and a suitable carrier or diluent therefor. The composition is preferably an insecticidal or acaricidal composition.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulfur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulfate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulfates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallization in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurized, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerization stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulfuric acid (for example sodium lauryl sulfate), salts of sulfonated aromatic compounds (for example sodium dodecylbenzenesulfonate, calcium dodecylbenzenesulfonate, butylnaphthalene sulfonate and mixtures of sodium di-isopropyl- and tri-isopropyl-naphthalene sulfonates), ether sulfates, alcohol ether sulfates (for example sodium laureth-3-sulfate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulfosuccinamates, paraffin or olefine sulfonates, taurates and lignosulfonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapor or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilizers (for example nitrogen-, potassium- or phosphorus-containing fertilizers). Suitable formulation types include granules of fertilizer. The mixtures preferably contain up to 25% by weight of the compound of formula (I).

The invention therefore also provides a fertilizer composition comprising a fertilizer and a compound of formula (I).

The compositions of this invention may contain other compounds having biological activity, for example micronutrients or compounds having fungicidal activity or which possess plant growth regulating, herbicidal, insecticidal, nematicidal or acaricidal activity.

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergize the activity or complement the activity (for example by increasing the speed of effect or overcoming repellency) of the compound of formula (I); or help to overcome or prevent the development of resistance to individual components. The particular additional active ingredient will depend upon the intended utility of the composition. Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, S-bioallethrin, fenfluthrin, prallethrin or 5-benzyl-3-furylmethyl-(E)-(1R,3S)-2,2-dimethyl-3-(2-oxothiolan-3-ylidenemethyl)cyclopropane carboxylate;

b) Organophosphates, such as profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;

c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;

d) Benzoyl ureas, such as diflubenzuron, triflumuron, hexaflumuron, flufenoxuron or chlorfluazuron;

e) Organic tin compounds, such as cyhexatin, fenbutatin oxide or azocyclotin;

f) Pyrazoles, such as tebufenpyrad and fenpyroximate;

g) Macrolides, such as avermectins or milbemycins, for example abamectin, emamectin benzoate, ivermectin, milbemycin, spinosad, azadirachtin or spinetoram;

h) Hormones or pheromones;

i) Organochlorine compounds, such as endosulfan (in particular alpha-endosulfan), benzene hexachloride, DDT, chlordane or dieldrin;

j) Amidines, such as chlordimeform or amitraz;

k) Fumigant agents, such as chloropicrin, dichloropropane, methyl bromide or metam;

l) Neonicotinoid compounds, such as imidacloprid, thiacloprid, acetamiprid, nitenpyram, dinotefuran, thiamethoxam, clothianidin, nithiazine or flonicamid;

m) Diacylhydrazines, such as tebufenozide, chromafenozide or methoxyfenozide;

n) Diphenyl ethers, such as diofenolan or pyriproxifen;

o) Indoxacarb;

p) Chlorfenapyr;

q) Pymetrozine;

r) Spirotetramat, spirodiclofen or spiromesifen;

s) Diamides, such as flubendiamide, chlorantraniliprole or cyantraniliprole;

t) Sulfoxaflor;

u) Metaflumizone;

v) Fipronil and Ethiprole; or w) Pyrifluqinazon.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of fungicidal compounds which may be included in the composition of the invention are (E)-N-methyl-2-[2-(2,5-dimethylphenoxymethyl)phenyl]-2-methoxy-iminoacetamide (SSF-129), 4-bromo-2-cyano-N,N-dimethyl-6-trifluoromethyl-benzimidazole-1-sulfonamide, α-[N-(3-chloro-2,6-xylyl)-2-methoxyacetamido]-γ-butyrolactone, 4-chloro-2-cyano-N,N-dimethyl-5-p-tolylimidazole-1-sulfonamide (IKF-916, cyamidazosulfamid), 3-5-dichloro-N-(3-chloro-1-ethyl-1-methyl-2-oxopropyl)-4-methylbenzamide (RH-7281, zoxamide), N-allyl-4,5,-dimethyl-2-trimethylsilylthiophene-3-carboxamide (MON65500), N-(1-cyano-1,2-dimethylpropyl)-2-(2,4-dichlorophenoxy)propionamide (AC382042), N-(2-methoxy-5-pyridyl)-cyclopropane carboxamide, acibenzolar (CGA245704), alanycarb, aldimorph, anilazine, azaconazole, azoxystrobin, benalaxyl, benomyl, biloxazol, bitertanol, blasticidin S, bromuconazole, bupirimate, captafol, captan, carbendazim, carbendazim chlorhydrate, carboxin, carpropamid, carvone, CGA41396, CGA41397, chinomethionate, chlorothalonil, chlorozolinate, clozylacon, copper containing compounds such as copper oxychloride, copper oxyquinolate, copper sulfate, copper tallate and Bordeaux mixture, cymoxanil, cyproconazole, cyprodinil, debacarb, di-2-pyridyl disulfide 1,1'-dioxide, dichlofluanid, diclomezine, dicloran, diethofencarb, difenoconazole, difenzoquat, diflumetorim, O,O-di-iso-propyl-S-benzyl thiophosphate, dimefluazole, dimetconazole, dimethomorph, dimethirimol, diniconazole, dinocap, dithianon, dodecyl dimethyl ammonium chloride, dodemorph, dodine, doguadine, edifenphos, epoxiconazole, ethirimol, ethyl-(Z)-N-benzyl-N-([methyl (methyl-thioethylideneaminooxycarbonyl)amino]thio)-β-alaninate, etridiazole, famoxadone, fenamidone (RPA407213), fenarimol, fenbuconazole, fenfuram, fenhexamid (KBR2738), fenpiclonil, fenpropidin, fenpropimorph, fentin acetate, fentin hydroxide, ferbam, ferimzone, fluazinam, fludioxonil, flumetover, fluoroimide, fluquinconazole, flusilazole, flutolanil, flutriafol, folpet, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb (SZX0722), isopropanyl butyl carbamate, isoprothiolane, kasugamycin, kresoxim-methyl, LY186054, LY211795, LY248908, mancozeb, maneb, mefenoxam, mepanipyrim, mepronil, metalaxyl, metconazole, metiram, metiram-zinc, metominostrobin, myclobutanil, neoasozin, nickel dimethyldithiocarbamate, nitrothal-isopropyl, nuarimol, ofurace, organomercury compounds, oxadixyl, oxasulfuron, oxolinic acid, oxpoconazole, oxycarboxin, pefurazoate, penconazole, pencycuron, phenazin oxide, phosetyl-Al, phosphorus acids, phthalide, picoxystrobin (ZA1963), polyoxin D, polyram, probenazole, prochloraz, procymidone, propamocarb, propiconazole, propineb, propionic acid, pyrazophos, pyrifenox, pyrimethanil, pyroquilon, pyroxyfur, pyrrolnitrin, quaternary ammonium compounds, quinomethionate, quinoxyfen, quintozene, sipconazole (F-155), sodium pentachlorophenate, spiroxamine, streptomycin, sulfur, tebuconazole, tecloftalam, tecnazene, tetraconazole, thiabendazole, thifluzamid, 2-(thiocyanomethylthio)benzothiazole, thiophanate-methyl, thiram, timibenconazole, tolclofos-methyl, tolylfluanid, triadimefon, triadimenol, triazbutil, triazoxide, tricyclazole, tridemorph, trifloxystrobin (CGA279202), triforine, triflumizole, triticonazole, validamycin A, vapam, vinclozolin, zineb and ziram.

The compounds of formula (I) may be mixed with soil, peat or other rooting media for the protection of plants against seed-borne, soil-borne or foliar fungal diseases.

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following Examples illustrate, but do not limit, the invention.

PREPARATION EXAMPLES

The following abbreviations were used throughout this section: s=singlet; bs=broad singlet; d=doublet; dd=double doublet; dt=double triplet; t=triplet; tt=triple triplet, q=quartet, sept=septet; m=multiplet; Me=methyl; Et=ethyl; Pr=propyl; Bu=butyl; RT=retention time; MH⁺=molecular cation.

Example I1

Preparation of 4-bromo-2-methyl-benzoic acid tert-butyl ester

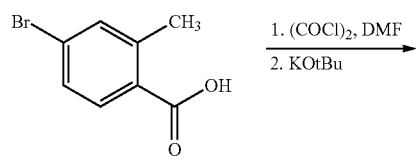

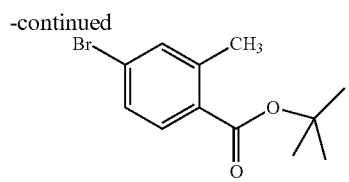

4-Bromo-2-methyl-benzoic acid (commercially available) (50 g) was suspended in dichloromethane (500 ml). A catalytic amount of N,N-dimethylformamide ("DMF") and oxalyl chloride (23 ml) were added to the suspension. The reaction mixture was stirred at ambient temperature for 3 hours. The reaction mixture was concentrated and the residue dissolved in dry tetrahydrofuran (800 ml). The solution was cooled to 2° C. and added to a solution of potassium tert-butoxide (39.2 g) in dry tetrahydrofuran (300 ml) dropwise at 5-10° C. The reaction mixture was stirred at ambient temperature for 30 minutes and then poured onto a mixture of ice and water. The mixture was extracted with ethyl acetate. The organic extract was washed with water, dried over sodium sulfate and concentrated to give 4-bromo-2-methyl-benzoic acid tert-butyl ester (65.3 g) as yellow oil. $^1$H-NMR (CDCl$_3$, 400 MHz): 7.70 (d, 1H), 7.40 (s, 1H), 7.35 (d, 1H), 2.58 (s, 3H), 1.60 (s, 9H).

Similarly, 4-bromo-N-butyl-2-methyl-benzamide was obtained when butylamine was used as reagent. $^1$H-NMR (CDCl$_3$, 400 MHz): 7.40-7.20 (m, 3H), 5.75 (1H, s), 3.45 (q, 2H), 2.45 (s, 3H), 1.60 (m, 2H), 1.40 (m, 2H), 0.95 (t, 3H).

Example I2

Preparation of 4-formyl-2-methyl-benzoic acid tert-butyl ester

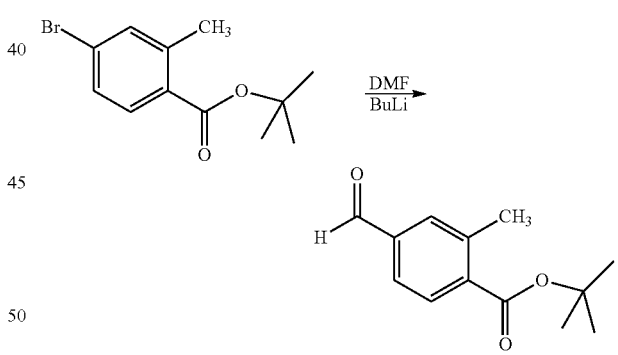

A solution of 4-bromo-2-methyl-benzoic acid tert-butyl ester (Example I1) (75 g) in dry tetrahydrofuran (750 ml) was cooled to −100° C. A solution of butyl lithium ("BuLi") (1.6 M in hexane) (163 ml) was added dropwise at −100° C. N,N-Dimethylformamide (1.14 ml) was added at −100° C. The reaction mixture was stirred at −95° C. for 75 minutes. The reaction was quenched by addition of aqueous ammonium chloride (saturated) (8 ml) at −90° C. The mixture was stirred for 10 minutes at −90° C., warmed to 0° C. and poured on a mixture of ice and water. The mixture was allowed to warm to ambient temperature and then extracted twice with ethyl acetate. The combined organic phases were washed with water, dried over sodium sulfate, and concentrated to give 4-formyl-2-methyl-benzoic acid tert-butyl ester (60.3 g)

as yellow oil. $^1$H-NMR (CDCl$_3$, 400 MHz): 10.03 (s, 1H), 7.93 (d, 1H), 7.75 (m, 2H), 2.65 (s, 3H), 1.65 (s, 9H).

Similarly, N-butyl-4-formyl-2-methyl-benzamide was obtained from 4-bromo-N-butyl-2-methyl-benzamide (Example I1). $^1$H-NMR (CDCl$_3$, 400 MHz): 10.00 (s, 1H), 7.75-7.45 (m, 3H), 5.75 (1H, s), 3.45 (m, 2H), 2.50 (s, 3H), 1.60 (m, 2H), 1.40 (m, 2H), 0.95 (t, 3H).

Example I3

Preparation of (4-tert-butoxycarbonyl-3-methyl-benzylidene)-N-methyl-nitrone

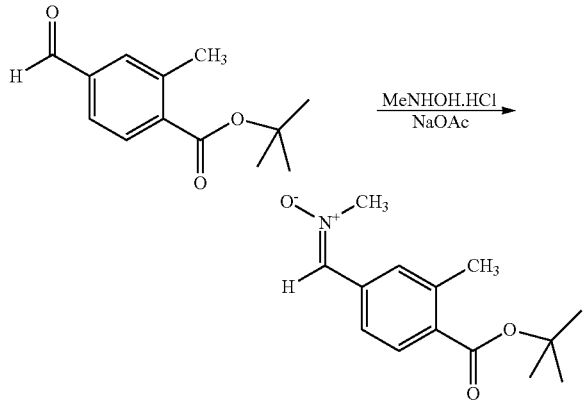

To a solution of 4-formyl-2-methyl-benzoic acid tert-butyl ester (Example I2) (1.57 g) in tetrahydrofuran/water (3:1) (20 ml) was added sodium acetate (0.67 g) and N-methylhydroxylamine hydrochloride (0.69 g). The reaction mixture was stirred at 50° C. for 15 hours. The reaction mixture was diluted with ethyl acetate and water. The phases were separated and the organic layer was washed with water, dried over sodium sulfate and concentrated. The residue was purified by column chromatography on silica gel (eluent: methanol/ethyl acetate 5:5) to give (4-tert-butoxycarbonyl-3-methyl-benzylidene)-N-methyl-nitrone (1.43 g) as yellow oil. $^1$H-NMR (CDCl$_3$, 400 MHz): 8.10 (s, 1H), 8.02 (d, 1H), 7.85 (d, 1H), 7.35 (s, 1H), 3.90 (s, 3H), 2.60 (s, 3H).

Similarly, (4-butylcarbamoyl-3-methyl-benzylidene)-N-phenylmethyl-nitrone was obtained from N-butyl-4-formyl-2-methyl-benzamide (Example I2) when N-phenylmethyl-hydroxylamine hydrochloride was used as reagent. $^1$H-NMR (CDCl$_3$, 400 MHz): 8.05 (s, 1H), 7.50-7.30 (m, 8H), 5.75 (1H, s), 5.05 (s, 2H), 3.45 (m, 2H), 2.45 (s, 3H), 1.55 (m, 2H), 1.40 (m, 2H), 0.95 (t, 3H).

Example I4

Preparation of 4-[5-(3,5-dichloro-phenyl)-2-methyl-5-trifluoromethyl-isoxazolidin-3-yl]-2-methyl-benzoic acid tert-butyl ester

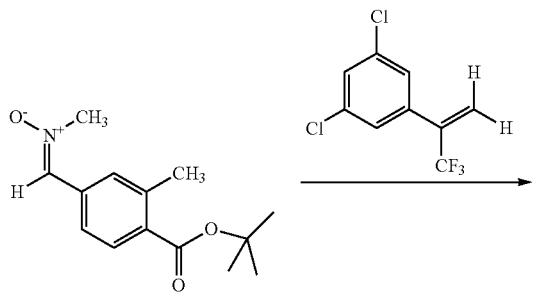

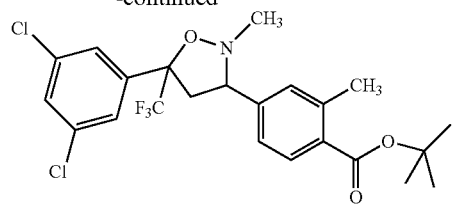

To a solution of (4-tert-butoxycarbonyl-3-methyl-benzylidene)-N-methyl-nitrone (Example I3) (1.42 g) in toluene (10 ml) was added 1,3-dichloro-5-(1-trifluoromethyl-vinyl)-benzene (2.17 g) (prepared according to WO 2005/085216). The reaction mixture was heated in a microwave at 120° C. for 3.5 hours. The toluene was evaporated and the residue was purified by column chromatography on silica gel (eluent: ethyl acetate/heptane 5:95 to 50:50) to give 4-[5-(3,5-dichloro-phenyl)-2-methyl-5-trifluoromethyl-isoxazolidin-3-yl]-2-methyl-benzoic acid tert-butyl ester as a mixture of diastereoisomers (1.73 g). $^1$H-NMR (CDCl$_3$, 400 MHz): 7.80-7.10 (m, 6H), 3.85-3.55 (m, 1H), 3.32-2.50 (m, 9H), 1.60 (m, 9H).

Similarly, 4-[5-(3,5-dichloro-phenyl)-5-methyl-2-phenylmethyl-isoxazolidin-3-yl]-N-butyl-2-methyl-benzamide (Compound No. A23 of Table A) was obtained from (4-butylcarbamoyl-3-methyl-benzylidene)-N-phenylmethyl-nitrone (Example I3). $^1$H-NMR (CDCl$_3$, 400 MHz): 7.40-7.15 (m, 11H), 5.65 (bs, 1H), 4.15-3.75 (m, 3H), 3.45 (m, 2H), 3.35-2.60 (m, 2H), 2.45 (s, 3H), 1.60 (m, 2H), 1.40 (m, 2H), 0.95 (m, 3H).

Example I5

Preparation 4-[5-(3,5-dichloro-phenyl)-2-methyl-5-trifluoromethyl-isoxazolidin-3-yl]-2-methyl-benzoic acid

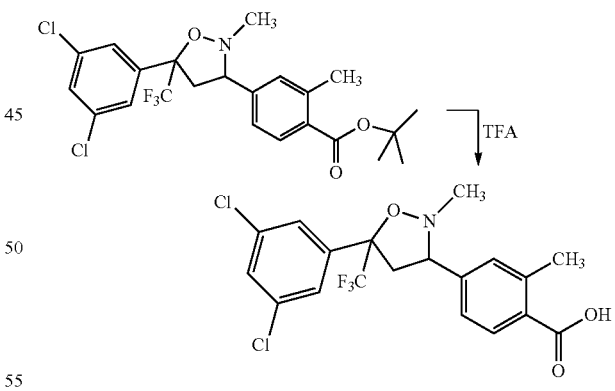

To a solution of 4-[5-(3,5-dichloro-phenyl)-2-methyl-5-trifluoromethyl-isoxazolidin-3-yl]-2-methyl-benzoic acid tert-butyl ester (Example I4) (0.67 g) in dichloromethane (15 ml) was added trifluoroacetic acid ("TFA") (1.05 ml). The reaction mixture was stirred at ambient temperature for 16 hours. The dichloromethane was evaporated and ethyl acetate was added. The mixture was washed with water, dried over sodium sulfate and concentrated. The residue was purified by preparative HPLC to give 4-[5-(3,5-dichloro-phenyl)-2-methyl-5-trifluoromethyl-isoxazolidin-3-yl]-2-methyl-benzoic acid as a mixture of diastereoisomers (0.56 g). $^1$H-NMR (CDCl₃, 400 MHz): 8.05 (m, 1H), 7.45-7.15 (m, 5H), 3.90-3.60 (m, 1H), 3.35-2.60 (m, 9H).

Example P1

Preparation of Compounds of Formula (I) from the Carboxylic Acid

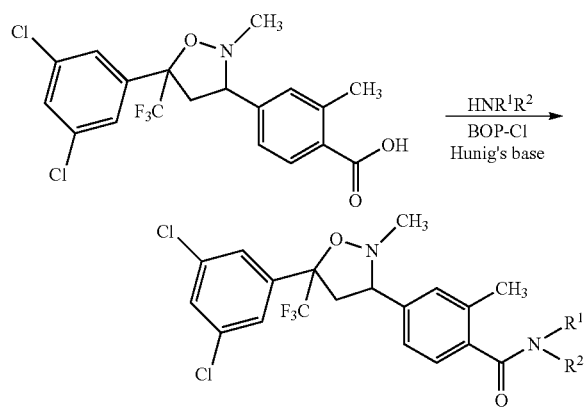

To a solution of carboxylic acid (30 μmol), for example 4-[5-(3,5-dichloro-phenyl)-2-methyl-5-trifluoromethyl-isoxazolidin-3-yl]-2-methyl-benzoic acid (Example I5) for Compound No. A2 of Table A, in N,N-dimethylacetamide ("DMA") (0.4 ml) was added successively a solution of an amine of formula HNR¹R² (36 μmol), for example but-2-ylamine for Compound No. A2 of Table A, in N,N-dimethylacetamide ("DMA") (0.15 ml), diisopropylethylamine (Hunig's Base) (0.04 ml), and a solution of bis(2-oxo-3-oxazolidinyl)-phosphonic chloride ("BOP-Cl") (15.3 mg) in N,N-dimethylacetamide ("DMA") (0.2 ml). The reaction mixture was stirred at 100° C. for 16 hours. Then the reaction mixture was diluted with acetonitrile (0.6 ml) and a sample was used for HPLC-MS analysis. The remaining mixture was further diluted with acetonitrile/N,N-dimethylformamide (4:1) (0.8 ml) and purified by HPLC. This method was used to prepare a number of compounds (Compound Nos. A1 to A22 of Table A) in parallel.

The Following Methods Were Used for HPLC-MS Analysis:

Method A (Agilent 1100er Series) with the following HPLC gradient conditions: Solvent A: 0.1% of formic acid in water; Solvent B: 0.1% of formic acid in acetonitrile.

| Time (minutes) | A (%) | B (%) | Flow rate (ml/min) |
|---|---|---|---|
| 0 | 80 | 20 | 1.7 |
| 2.5 | 0 | 100 | 1.7 |
| 2.8 | 0 | 100 | 1.7 |
| 2.9 | 80 | 20 | 1.7 |

Type of column: Waters atlantis dc18; Column length: 20 mm; Internal diameter of column: 3 mm; Particle Size: 3 micron; Temperature: 40° C.

Method B (Agilent) quaternary HPLC pump HP1100, HP1100 Diodearray Detektor, HP1100 thermostatted column compartment and HP1100 solvent degasser.

Solvent A: water with 0.04% HCOOH; Solvent B: Acetonitril/Methanol (4:1, v/v)+0.05% HCOOH.

| Time (minutes) | A (%) | B (%) | Flow rate (ml/min) |
|---|---|---|---|
| 0.00 | 95.0 | 5.0 | 1.7 |
| 2.00 | 0.0 | 100.0 | 1.7 |
| 2.80 | 0.0 | 100.0 | 1.7 |
| 2.90 | 95.0 | 5.0 | 1.7 |
| 3.10 | 95.0 | 5.0 | 1.7 |

Type of column: Phenomenex Gemini C18; Column length: 30 mm; Internal diameter of column: 3 mm; Particle Size: 3 micron; Temperature: 60° C.

TABLE A

Table A provides compounds of formula (Ia) wherein $G^1$ is oxygen, $R^3$ is trifluoromethyl, $R^4$ is 3,5-dichloro-phenyl-, $R^{5a}$ and $R^{5b}$ are both hydrogen, $R^7$ is methyl, and $R^1$, $R^2$ and $R^6$ have the values listed in the table below.

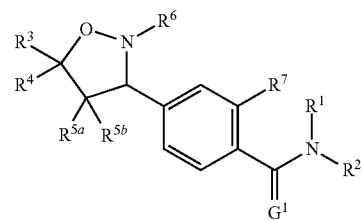

(Ia)

| Compound No. | R¹ | R² | R⁶ | RT (min) | MH⁺ | HPLC-MS Method |
|---|---|---|---|---|---|---|
| A1 | H | 1-oxo-thietan-3-yl- | methyl- | 3.17 | 520.1 | A |
| A2 | H | but-2-yl- | methyl- | 4.00 | 489.1 | A |
| A3 | H | 2,2,2-trifluoro-ethyl- | methyl- | 3.96 | 515.0 | A |
| A4 | H | ethyl- | methyl- | 3.66 | 460.9 | A |
| A5 | H | 1-methoxy-prop-2-yl- | methyl- | 3.76 | 504.9 | A |
| A6 | H | (1H-benzimidazol-2-yl)-methyl- | methyl- | 2.86 | 562.9 | A |
| A7 | H | 3,3,3-trifluoro-propyl- | methyl- | 3.98 | 528.9 | A |
| A8 | H | (tetrahydrofuran-2-yl)-methyl- | methyl- | 3.80 | 516.9 | A |
| A9 | H | (2-fluoro-phenyl)-methyl- | methyl- | 4.12 | 540.9 | A |
| A10 | H | 1-phenyl-eth-1-yl- | methyl- | 4.16 | 536.9 | A |
| A11 | H | (4-methoxy-phenyl)-methyl- | methyl- | 4.03 | 552.9 | A |
| A12 | H | 1,1-dioxo-thietan-3-yl- | methyl- | 3.51 | 536.9 | A |
| A13 | H | (2-chloro-pyrid-5-yl)-methyl- | methyl- | 3.80 | 557.9 | A |
| A14 | H | 3-fluoro-phenyl- | methyl- | 4.28 | 526.9 | A |
| A15 | H | 1,3-dimethyl-1H-pyrazol-5-yl- | methyl- | 3.76 | 526.9 | A |
| A16 | H | 4-methyl-thiazol-2-yl- | methyl- | 4.12 | 529.9 | A |
| A17 | H | 3-methyl-thietan-3-yl- | methyl- | 4.04 | 518.9 | A |
| A18 | H | 2-methyl-1-methylthio-prop-2-yl- | methyl- | 4.26 | 534.9 | A |
| A19 | H | thietan-3-yl- | methyl- | 3.86 | 504.9 | A |
| A20 | H | bicyclo[2.2.1]-heptan-2-yl- | methyl- | 4.28 | 526.9 | A |
| A21 | H | cyclobutyl- | methyl- | 3.92 | 486.9 | A |
| A22 | H | butyl- | methyl- | 2.18 | 489.0 | A |
| A23 | H | butyl- | phenyl-methyl- | 2.35 | 565.0 | B |

BIOLOGICAL EXAMPLES

This Example illustrates the insecticidal and acaricidal properties of compounds of formula (I). The tests were performed as follows:

*Spodoptera littoralis* (Egyptian Cotton Leafworm):

Cotton leaf discs were placed on agar in a 24-well microtiter plate and sprayed with test solutions at an application rate of 200 ppm. After drying, the leaf discs were infested with 5 L1 larvae. The samples were checked for mortality, feeding behavior, and growth regulation 3 days after treatment (DAT).

The following compound gave at least 80% control of Spodoptera littoralis: A1, A2, A3, A4, A7, A8, A9, A10, A11, A12, A13, A14, A16, A19, A21, A22.

*Heliothis virescens* (Tobacco Budworm):

Eggs (0-24 h old) were placed in 24-well microtiter plate on artificial diet and treated with test solutions at an application rate of 200 ppm (concentration in well 18 ppm) by pipetting. After an incubation period of 4 days, samples were checked for egg mortality, larval mortality, and growth regulation.

The following compound gave at least 80% control of Heliothis virescens: A1, A3, A9, A10, A11, A12, A13, A19.

*Plutella xylostella* (Diamond Back Moth):

24-well microtiter plate (MTP) with artificial diet was treated with test solutions at an application rate of 200 ppm (concentration in well 18 ppm) by pipetting. After drying, the MTP's were infested with L2 larvae (7-12 per well). After an incubation period of 6 days, samples were checked for larval mortality and growth regulation.

The following compound gave at least 80% control of Plutella xylostella: A1, A2, A3, A4, A5, A6, A7, A9, A10, A11, A12, A13, A14, A16, A17, A19, A21, A22, A23.

*Diabrotica balteata* (Corn Root Worm):

A 24-well microtiter plate (MTP) with artificial diet was treated with test solutions at an application rate of 200 ppm (concentration in well 18 ppm) by pipetting. After drying, the MTP's were infested with L2 larvae (6-10 per well). After an incubation period of 5 days, samples were checked for larval mortality and growth regulation.

The following compound gave at least 80% control of Diabrotica balteata: A1, A9, D12, A19.

*Thrips tabaci* (Onion Thrips):

Sunflower leaf discs were placed on agar in a 24-well microtiter plate and sprayed with test solutions at an application rate of 200 ppm. After drying, the leaf discs were infested with an aphid population of mixed ages. After an incubation period of 7 days, samples were checked for mortality.

The following compounds gave at least 80% control of Thrips tabaci: A1, A2, A3, A4, A7, A8, A9, A10, A11, A12, A13, A19, A20, A21, A23.

*Tetranychus urticae* (Two-Spotted Spider Mite):

Bean leaf discs on agar in 24-well microtiter plates were sprayed with test solutions at an application rate of 200 ppm. After drying, the leaf discs are infested with mite populations of mixed ages. 8 days later, discs are checked for egg mortality, larval mortality, and adult mortality.

The following compound gave at least 80% control of Tetranychus urticae: A1, A2, A3, A4, A5, A7, A8, A9, A10, A11, A12, A13, A15, A17, A19, A21, A22.

The invention claimed is:
1. A compound of formula (I)

wherein
$A^1$, $A^2$, $A^3$ and $A^4$ are independently of each other C—H, C—$R^7$, or nitrogen;
$G^1$ is oxygen or sulfur;
$R^1$ is hydrogen, $C_1$-$C_8$alkyl, $C_1$-$C_8$alkoxy-, $C_1$-$C_8$alkylcarbonyl-, or $C_1$-$C_8$alkoxycarbonyl-;
$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene-wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, or heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^{5a}$ and $R^{5b}$ are both hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$, aryl or aryl substituted by one to five $R^{14}$, or heterocyclyl or heterocyclyl substituted by one to five $R^{14}$;
each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^8$ and $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^9$ and $R^{13}$ is independently halogen or $C_1$-$C_8$alkyl;
each $R^{10}$, $R^{11}$ and $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;

each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-; or a salt or N-oxide thereof.

2. A compound according to claim 1 wherein $A^1$ is C—$R^7$, $A^2$ is C—H, $A^3$ is C—H or nitrogen and $A^4$ is C—H or nitrogen.

3. A compound according to claim 1 wherein $G^1$ is oxygen.

4. A compound according to claim 1 wherein $R^1$ is hydrogen, methyl, ethyl, methylcarbonyl-, or methoxycarbonyl-.

5. A compound according to claim 1 wherein $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, aryl-$C_1$-$C_4$alkylene- or aryl-$C_1$-$C_4$alkylene- wherein the aryl moiety is substituted by one to five $R^{10}$, heterocyclyl-$C_1$-$C_4$alkylene- or heterocyclyl-$C_1$-$C_4$alkylene- wherein the heterocyclyl moiety is substituted by one to five $R^{10}$, aryl or aryl substituted by one to five $R^{10}$, heterocyclyl or heterocyclyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene, wherein each aryl group is a phenyl group and each heterocycle group is selected from 1,2,3 triazolyl, 1,2,4 triazolyl, tetrazolyl, pyrimidinyl, pyrazinyl, pyridazinyl, tetrahydrothiophenyl, isoxazolinyl, pyridyl, tetrahydrofuranyl, imidazolyl, pyrazolyl, pyrrolyl, thiazolyl, oxetanyl, thietanyl, oxo-thietanyl and dioxo-thietanyl.

6. A compound according to claim 1 wherein $R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene-wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$.

7. A compound according to claim 1 wherein $R^3$ is chlorodifluoromethyl or trifluoromethyl.

8. A compound according to claim 1 wherein $R^4$ is aryl or aryl substituted by one to five $R^{11}$.

9. A compound according to claim 1 wherein $R^6$ is $C_1$-$C_8$alkyl.

10. A compound according to claim 1, wherein $A^1$ is C—$R^7$, $A^2$ is C—H, $A^3$ is C—H and $A^4$ is C—H;

$G^1$ is oxygen;

$R^1$ is hydrogen, methyl or ethyl;

$R^2$ is $C_1$-$C_8$alkyl or $C_1$-$C_8$alkyl substituted by one to five $R^8$, $C_3$-$C_{10}$cycloalkyl or $C_3$-$C_{10}$cycloalkyl substituted by one to five $R^9$, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, oxetanyl or oxetanyl substituted by one to five $R^{10}$, thietanyl or thietanyl substituted by one to five $R^{10}$, oxo-thietanyl or oxo-thietanyl substituted by one to five $R^{10}$, or dioxo-thietanyl or dioxo-thietanyl substituted by one to five $R^{10}$, $C_1$-$C_8$alkylaminocarbonyl-$C_1$-$C_4$ alkylene, $C_1$-$C_8$haloalkylaminocarbonyl-$C_1$-$C_4$ alkylene, or $C_3$-$C_8$cycloalkyl-aminocarbonyl-$C_1$-$C_4$ alkylene;

$R^3$ is chlorodifluoromethyl or trifluoromethyl;

$R^4$ is 3,5-dibromo-phenyl-, 3,5-dichloro-phenyl-, 3,5-bis-(trifluoromethyl)-phenyl-, 3,4-dichloro-phenyl-, 3,4,5-trichloro-phenyl- or 3-trifluoromethyl-phenyl- $R^{5a}$ and $R^{5b}$ are hydrogen;

$R^6$ is $C_1$-$C_8$alkyl or $C_1$-$C_8$alkyl substituted by one to five $R^{12}$, phenyl-$C_1$-$C_4$alkylene- or phenyl-$C_1$-$C_4$alkylene- wherein the phenyl moiety is substituted by one to five $R^{14}$, $R^7$ is independently bromo, chloro, fluoro, cyano, nitro, methyl, ethyl, trifluoromethyl, vinyl, methoxy, difluoromethoxy, or trifluoromethoxy;

each $R^8$ is independently bromo, chloro, fluoro, methoxy, or methylthio;

each $R^9$ is methyl;

each $R^{10}$ is independently bromo, chloro, fluoro, cyano, nitro, methyl, ethyl, trifluoromethyl, methoxy, difluoromethoxy, or trifluoromethoxy;

each $R^{12}$ is independently bromo, chloro, fluoro, methoxy, or methylthio;

each $R^{14}$ is independently bromo, chloro, fluoro, cyano, nitro, methyl, ethyl, trifluoromethyl, methoxy, difluoromethoxy, or trifluoromethoxy.

11. A compound according to claim 1, wherein $A^1$ is C—$R^7$, $A^2$ is C—H, $A^3$ is C—H and $A^4$ is C—H;

$G^1$ is oxygen;

$R^1$ is hydrogen;

$R^2$ is $C_1$-$C_8$alkyl or $C_1$-$C_8$alkyl substituted by one to three halogen atoms, $C_3$-$C_{10}$cycloalkyl or $C_3$-$C_{10}$cycloalkyl substituted by one or two methyl groups, phenyl-$C_1$-$C_4$alkylene- or phenyl-$C_1$-$C_4$alkylene- wherein the phenyl moiety is substituted by one to five $R^{10}$, pyridyl-$C_1$-$C_4$alkylene- or pyridyl-$C_1$-$C_4$alkylene- wherein the pyridyl moiety is substituted by one to four $R^{10}$, thietanyl, oxo-thietanyl or dioxo-thietanyl;

$R^3$ is trifluoromethyl;

$R^4$ is 3,5-dichloro-phenyl;

$R^{5a}$ and $R^{5b}$ are hydrogen;

$R^6$ is $C_1$-$C_8$alkyl;

$R^7$ is methyl each $R^{10}$ is independently bromo, chloro, fluoro, cyano or methyl.

12. A method of controlling insects, acarines, nematodes or molluscs which comprises applying to a pest, to a locus of a pest, or to a plant susceptible to attack by insects, acarines, nematodes or molluscs, an insecticidally, acaricidally, nematicidally or molluscicidally effective amount of a compound of formula (I) as defined in claim 1.

13. An insecticidal, acaricidal, nematicidal or molluscicidal composition comprising an insecticidally, acaricidally, nematicidally or molluscicidally effective amount of a compound of formula (I) as defined in claim 1.

14. An insecticidal, acaricidal, nematicidal or molluscicidal composition according to claim 13 comprising an additional compound having biological activity.

15. A compound of formula (II)

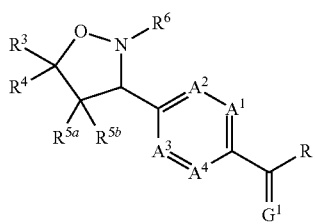

$A^1$, $A^2$, $A^3$ and $A^4$ are independently of each other C—H, C—$R^7$, or nitrogen;
$R^3$ is $C_1$-$C_8$haloalkyl;
$R^4$ is aryl or aryl substituted by one to five $R^{11}$, or heteroaryl or heteroaryl substituted by one to five $R^{11}$;
$R^{5a}$ and $R^{5b}$ are both hydrogen;
$R^6$ is hydrogen, $C_1$-$C_8$alkyl or $C_1$-$C_8$alkyl substituted by one to five $R^{12}$, $C_3$-$C_{10}$cycloalkyl or $C_3$-$C_{10}$cycloalkyl substituted by one to five $R^{13}$, aryl-$C_1$-$C_4$alkylene- or aryl-$C_1$-$C_4$alkylene- wherein the aryl moiety is substituted by one to five $R^{14}$, heterocyclyl-$C_1$-$C_4$alkylene- or heterocyclyl-$C_1$-$C_4$alkylene- wherein the heterocyclyl moiety is substituted by one to five $R^{14}$, aryl or aryl substituted by one to five $R^{14}$, or heterocyclyl or heterocyclyl substituted by one to five $R^{14}$;
each $R^7$ is independently halogen, cyano, nitro, $C_1$-$C_8$alkyl, $C_1$-$C_8$haloalkyl, $C_1$-$C_8$alkenyl, $C_1$-$C_8$haloalkenyl, $C_1$-$C_8$alkynyl, $C_1$-$C_8$haloalkynyl, $C_3$-$C_{10}$cycloalkyl, $C_1$-$C_8$alkoxy-, $C_1$-$C_8$haloalkoxy-, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^{12}$ is independently halogen, cyano, nitro, hydroxy, $C_1$-$C_8$alkoxy-, $C_1$-$C_8$haloalkoxy-, $C_1$-$C_8$alkylcarbonyl-, $C_1$-$C_8$alkoxycarbonyl-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, or $C_1$-$C_8$haloalkylsulfonyl-;
each $R^{13}$ is independently halogen or $C_1$-$C_8$alkyl;
each $R^{14}$ is independently halogen, cyano, nitro, $C_1$-$C_8$alkyl, $C_1$-$C_8$haloalkyl, $C_2$-$C_8$alkenyl, $C_2$-$C_8$haloalkenyl, $C_2$-$C_8$alkynyl, $C_2$-$C_8$haloalkynyl, hydroxy, $C_1$-$C_8$alkoxy-, $C_1$-$C_8$haloalkoxy-, mercapto, $C_1$-$C_8$alkylthio-, $C_1$-$C_8$haloalkylthio-, $C_1$-$C_8$alkylsulfinyl-, $C_1$-$C_8$haloalkylsulfinyl-, $C_1$-$C_8$alkylsulfonyl-, $C_1$-$C_8$haloalkylsulfonyl-, $C_1$-$C_8$alkylcarbonyl-, $C_1$-$C_8$alkoxycarbonyl-, aryl or aryl substituted by one to five $R^{15}$, or heterocyclyl or heterocyclyl substituted by one to five $R^{15}$;
each $R^{15}$ is independently halogen, cyano, nitro, $C_1$-$C_4$alkyl, $C_1$-$C_4$haloalkyl, $C_1$-$C_4$alkoxy-, or $C_1$-$C_4$haloalkoxy-; or a salt or N-oxide thereof,
$G^1$ is oxygen, and R is hydroxy, $C_1$-$C_6$alkoxy or halogen; or a salt or N-oxide thereof.

* * * * *